United States Patent
Blake et al.

(10) Patent No.: US 12,033,051 B2
(45) Date of Patent: Jul. 9, 2024

(54) MACHINE LEARNING BASED RECONSTRUCTION OF INTRACARDIAC ELECTRICAL BEHAVIOR BASED ON ELECTROCARDIOGRAMS

(71) Applicant: Lawrence Livermore National Security, LLC, Livermore, CA (US)

(72) Inventors: Robert C. Blake, Mountain House, CA (US); Thomas J. O'Hara, Alameda, CA (US); Mikel L. Landajuela, Dublin, CA (US); Rushil Anirudh, Dublin, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 504 days.

(21) Appl. No.: 17/103,624

(22) Filed: Nov. 24, 2020

(65) Prior Publication Data

US 2021/0193291 A1 Jun. 24, 2021

Related U.S. Application Data

(60) Provisional application No. 62/950,885, filed on Dec. 19, 2019.

(51) Int. Cl.
*G06N 3/04* (2023.01)
*A61B 5/327* (2021.01)
(Continued)

(52) U.S. Cl.
CPC ............... *G06N 3/04* (2013.01); *A61B 5/327* (2021.01); *A61B 5/367* (2021.01); *G06N 3/08* (2013.01); *G16H 50/20* (2018.01); *G16H 50/50* (2018.01)

(58) Field of Classification Search
CPC . G06N 3/04; G06N 3/08; A61B 5/327; A61B 5/367; G16H 50/20; G16H 50/50
See application file for complete search history.

(56) References Cited

U.S. PATENT DOCUMENTS

| 10,319,144 B2 | 6/2019 | Krummen et al. |
| 2016/0262635 A1 | 9/2016 | McCullouch et al. |

(Continued)

OTHER PUBLICATIONS

Kachenoura et al., Comparison of four estimators of the 3D cardiac electrical activity for surface ECG synthesis from intracardiac recordings, 2009 IEEE International Conference on Acoustics, Speech and Signal Processing 485-488 (Year: 2009).*

(Continued)

*Primary Examiner* — Jordan L Jackson
(74) *Attorney, Agent, or Firm* — Knobbe, Martens, Olson & Bear, LLP

(57) ABSTRACT

A computer-based system and process are disclosed for reconstructing the internal electrical behavior of a patient's heart based partly or wholly on the patient's electrocardiogram (ECG). The output of the process may include, for example, a cardiac activation map, and/or a representation of transmembrane potentials over time. The process advantageously does not require any medical imaging of the patient, and does not require any special medical equipment. For example, the patient's activation map and transmembrane potentials may be reconstructed based solely on a preexisting or newly-obtained 12-lead cardiac ECG of the patient. The process makes use of a machine learning model, such as a neural network based model, trained with actual and/or simulated ECGs and intracardiac electrical data (typically transmembrane potentials) of many thousands of patients. Because an insufficient quantity of such data exists for actual patients, model training may be performed using ECGs and (Continued)

intracardiac electrical data obtained through computer simulations.

17 Claims, 12 Drawing Sheets

(51) Int. Cl.
*A61B 5/367* (2021.01)
*G06N 3/08* (2023.01)
*G16H 50/20* (2018.01)
*G16H 50/50* (2018.01)

(56) References Cited

U.S. PATENT DOCUMENTS

| | | | |
|---|---|---|---|
| 2017/0161896 A1 | 6/2017 | Blake, III | |
| 2017/0178403 A1 | 6/2017 | Krummen et al. | |
| 2017/0209698 A1 | 6/2017 | Villongco et al. | |
| 2017/0330075 A1* | 11/2017 | Tuysuzoglu | G16H 50/50 |
| 2019/0206127 A1 | 7/2019 | Krummen et al. | |
| 2019/0304183 A1 | 10/2019 | Krummen et al. | |

OTHER PUBLICATIONS

Porée et al., Surface Electrocardiogram Reconstruction From Intracardiac Electrograms Using a Dynamic Time Delay Artificial Neural Network, 60(1) IEEE Transactions On Biomed Engineering 106-114 (Jan. 2013) (Year: 2013).*

Yang et al., Localization of Origins of Premature Ventricular Contraction by Means of Convolutional Neural Network From 12-Lead ECG, 65(7) IEEE Transactions on Biomed Engineering 1662-1671 (Jul. 2018) (Year: 2018).*

Cantwell et al., Rethinking multiscale cardiac electrophysiology with machine learning and predictive modelling, 104 Computers in Bio and Med 339-351 (Jan. 2019) (Year: 2019).*

Giffard-Roisin et al., Noninvasive Personalization of a Cardiac Electrophysiology Model From Body Surface Potential Mapping, 64(9) IEEE Transactions on Biomed Engineering 2206-2218 (Sep. 2017) (Year: 2017).*

Rajan et al., Generalization Studies of Neural Network Models for Cardiac Disease Detection Using Limited Channel ECG, IBM Research (Jan. 5, 2019) (Year: 2019).*

Karoui, Amel, et al., "Direct Mapping from Body Surface Potentials to Cardiac Activation Maps Using Neural Networks," 2019.

Bayer, J.D., et al., "A Novel Rule-Based Algorithm for Assigning Myocardial Fiber Orientation to Computational Heart Models," Ann Biomed Eng., Oct. 2012.

* cited by examiner

MACHINE LEARNING BASED RECONSTRUCTION OF INTRACARDIAC ELECTRICAL BEHAVIOR BASED ON ELECTROCARDIOGRAMS

PRIORITY CLAIM

This application claims the benefit of U.S. Provisional Appl. No. 62/950,885, filed Dec. 19, 2019, the disclosure of which is hereby incorporated by reference.

STATEMENT REGARDING FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND OF THE INVENTION

Technical Field

The present invention relates to computer-based processes and procedures for reconstructing intracardiac electrical behavior.

Description of the Related Art

Sudden cardiac death (SCD) claims the lives of tens of millions of victims annually worldwide. Most SCD is due to abnormal electrical patterns called arrhythmias. Arrhythmias are initiated by portions of cardiac tissue that erroneously or spontaneously activate during an inappropriate point in the cardiac cycle, resulting in a self-perpetuating constant contraction (fibrillation) that stops the heart from pumping enough blood to the brain. The current standard of care for patients at risk of ventricular fibrillation involves antiarrhythmic drugs and the implantable cardioverter defibrillator (ICD). Neither can prevent ventricular fibrillation; rather, they attempt to suppress it (with drugs) and deliver defibrillation shocks to prevent death (with a defibrillator).

A third approach for treating SCD is radio-frequency ablation therapy. This involves navigating a catheter into the ventricular chambers via veins or arteries and cauterizing the tissue that initiates abnormal electrical activity. When this procedure works, it is an out-patient procedure that permanently treats the underlying cause of SCD. For atrial fibrillation this procedure is very effective and considered standard of care. Unfortunately, for ventricular fibrillation the procedure has limited success, with only 58% efficacy after one procedure and 71% efficacy for multiple repeat procedures.

The efficacy of RF ablation therapy relies heavily on the ability to accurately identify the cardiac tissue that is the source of the arrhythmia. A common procedure for identifying such tissue, and for analyzing the electrical behavior of the cardiac tissue generally, is an intracardiac electrogram. This procedure involves introducing a catheter with a magnetic tip into the heart, and using a magnetic guidance system outside the patient's body to monitor and record the tip's location as the tip is used to take electrical measurements at selected locations. Typically, the intracardiac electrogram procedure lasts for about 2 hours. The data collected through this process is typically displayed to clinicians as a cardiac activation map.

Because intracardiac electrograms are expensive and burdensome, attempts have been made to collect or generate similar data through non-invasive procedures. One such non-invasive procedure is non-invasive electrocardiographic imaging, or ECGi. This procedure ordinarily requires the patient to wear a costly multi-electrode, one-time-use vest, and to obtain a CT scan or MRI to register electrode, torso and heart surface geometries. Thus, the procedure is time consuming and expensive, and is not suitable for all patients. Further, ECGi is not useful for reconstructing interior electrical potentials within the myocardium.

SUMMARY

A computer-based system and process are disclosed for reconstructing the internal electrical behavior of a patient's heart based partly or wholly on the patient's electrocardiogram (ECG). The output of the process may include a cardiac activation map and/or an image or other representation of the transmembrane potentials within the heart. The process advantageously does not require any medical imaging (CT, MRI, PET, X-ray, etc.) of the patient, and does not require any special medical equipment. For example, the patient's activation map and transmembrane potentials may be reconstructed based solely on a preexisting or newly-obtained 12-lead cardiac ECG of the patient. The process makes use of a machine learning model, such as a neural network based model, trained with actual and/or simulated ECGs and intracardiac electrical behavior data (e.g., transmembrane potentials) of many thousands of patients. Because an insufficient quantity of such data exists for actual patients, the process preferably uses ECGs and intracardiac electrical behavior data obtained through computer simulations.

Neither this summary nor the following detailed description purports to define the invention. The invention is defined by the claims.

BRIEF DESCRIPTION OF THE DRAWINGS

The following drawings illustrate certain embodiments of the invention, do not limit the invention's scope.

DETAILED DESCRIPTION OF THE PREFERRED EMBODIMENTS

Specific embodiments will now be described with reference to the drawings. These embodiments are intended to illustrate, and not limit, the invention. The scope of the invention is defined by the claims.

1. OVERVIEW

Figure 1:
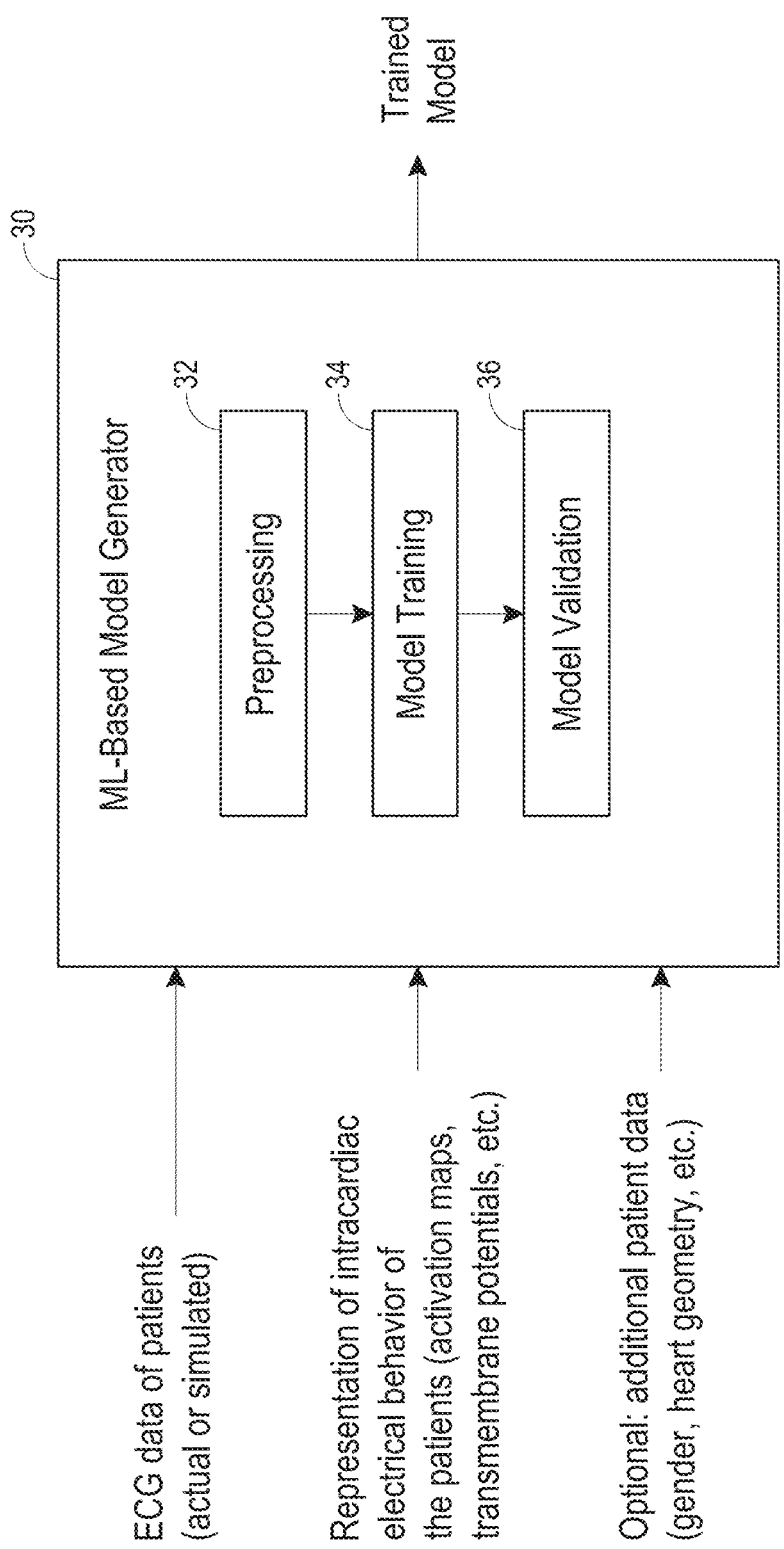
FIG. 1 illustrates a process for training a machine learning model to reconstruct intracardiac electrical activity according to one embodiment.

FIG. 1 illustrates the general process by which a model is trained to reconstruct or predict intracardiac electrical behavior from electrocardiogram (ECG) data according to a preferred embodiment. The machine learning (ML) based model generator block 30 in FIG. 1 represents a computing system programmed and configured to use known machine learning processes to generate model parameters (e.g., weights) based on training data. The model preferably, but not necessarily, includes or consists of a neural network having multiple layers.

As illustrated, the model is trained using two primary types of data: (1) ECGs (actual and/or simulated) of patients, and (2) intracardiac electrical behavioral data (actual and/or simulated) of the patients. The ECG data is preferably 12-lead ECG data, although other types of ECGs may be used. The intracardiac electrical behavioral data may include data representing the progression of transmembrane potentials, activation events and repolarization events, over time. The intracardiac electrical behavior data may be provided in any of a variety of formats (activation maps, images showing transmembrane potentials, simulator-specific file formats, etc.).

To adequately train the model, the actual and/or simulated data of many thousands (and ideally hundreds of thousands) of human subjects of varying characteristics is used. Because no known databases exist that contain a sufficiently large quantity of actual ECGs and corresponding intracardiac electrical data, the model is preferably trained primarily or exclusively using data generated through simulations of cardiac behavior. A preferred process by which such simulated data is generated is described below under the heading "Simulation-based generation of training data." Where the model is trained using both actual and simulated data, a greater amount of weight may be given to the actual data during training, such that the actual data has a greater influence on the model weights than the simulated data.

As illustrated by the lower input arrow of FIG. 1, one or more additional types of patient data may optionally be provided to the ML-based model generator 30 during training. Examples include gender, heart geometry, heart volume, heart orientation, patient images, clinical distance measurements of the placement of internal organs, and data collected by vest-electrode systems such as CardioInsight™. Where provided, the trained model may be capable of using these types of information of the actual patient (together with the patient's ECG) to reconstruct the patient's intracardiac electrical behavior. Additionally or alternatively, different models may be generated for different classes of human subjects (e.g., male versus female). Different models may also be generated for reconstructing/predicting different types of intracardiac electrical behavior (e.g., activation maps versus transmembrane voltages).

As illustrated in FIG. 1, the model generator 30 performs three primary tasks: preprocessing 32, model training 34, and model validation 36. The preprocessing task 32 involves transforming the input data into a form amenable to machine learning. This may involve some or all of the following: (1) normalizing the ECGs (e.g., such that the baseline is at 0 and the maximum deflection from 0 is normalized to 1, as helpful to account for ECG error and to account for variances in patient torso conductivity), (2) separation of the atrial, purkinje fibers, and ventricular contributions from the ECGs, and (3) wavelet decomposition of the ECGs. The preprocessing task also preferably involves feature extraction from ECGs and intracardiac electrical behavior data. Examples of ECG features that may be extracted include duration of the QT interval, QRS width, whether the T wave is inverted, and data values generated from wavelet decomposition of the ECG. Examples of intracardiac electrical behavior features that may be extracted include, for specific cardiac locations, activation time, repolarization time, activation potential duration, and local conduction velocity. Some extracted features may be represented as vectors. If the optional "additional patient data" shown in FIG. 1 is provided, preprocessing may also be applied to some or all of this data; for example, if patient images are available, they may be segmented as described below in the section on simulation.

The model training task 34 involves the application of known machine learning processes to detect correlations between the ECGs and intracardiac electrical behavior, including correlations between the extracted ECG features and the extracted intracardiac electrical behavior features. For example, in the case of a neural network, during each iteration, the ECG features of an actual or simulated ECG may be provided to the neural network's input layer while the corresponding (actual or simulated) intracardiac electrical behavior features are provided to the neural network's output layer; the weights applied by intermediate nodes of the neural network may then be updated reflect correlations between these two feature sets. If one or more additional types of patient data (e.g., gender, heart geometry) are provided as shown in FIG. 1, they may be provided to the input layer as additional features. In addition, these additional data types may optionally be used to train the model to predict or estimate other characteristics of the patient, such as heart geometry, heart orientation, etc. from the patient's ECG. Any of a variety of machine learning networks may be used, such as sequence to sequence networks, feed forward networks and recurrent neural networks.

As described below in the section describing experimentation and test results, one trained model may be generated for reconstructing an activation map, and another trained model may be generated for the more complex task of reconstructing transmembrane voltages. (Note that an activation map may be generated from the transmembrane voltages.) The former may be used where activation map reconstruction is all that is needed, and the latter may be used where a complete temporal reconstruction of the depolarization and repolarization phases is desired.

The model validation task 36 involves testing the trained model against a portion of the input patient data not used for model training. Specifically, the database of input patient data may be divided into a training portion and a validation portion, and the validation portion may be used to evaluate the extent to which the trained model can predict or infer the intracardiac electrical behavior of patients in the validation portion. Preferably, actual (non-simulated) ECG and intracardiac electrical behavior data are included in the validation portion to account for possible inaccuracies introduced by simulation. A trained model may be accepted or rejected during this process based on the accuracy of its predictions. As is known in the art, various parameters used for model generation (e.g., neural network architecture, features to extract, etc.) may be varied to improve model accuracy. Examples of neural network architectures that may be used include sequence-to-sequence neural networks, recurrent neural networks, convolutional neural networks, and WaveNet. Machine learning models other than neural networks may alternatively be used.

Figure 2:
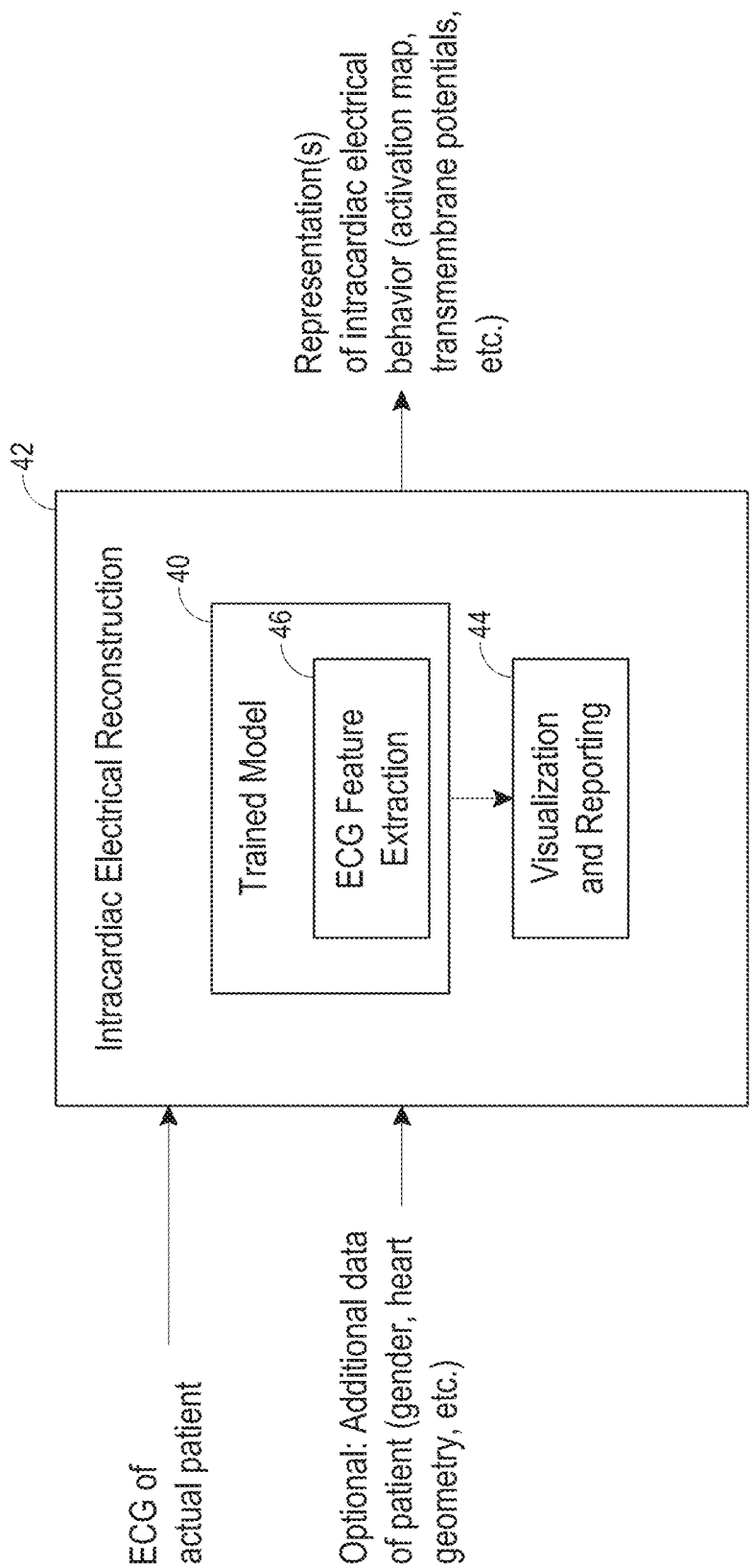
FIG. 2 illustrates how a trained model generated using the process of FIG. 1 may be used in a clinical environment in one embodiment.

As illustrated in FIG. 2, once a trained model 40 is generated, it may be used to generate one or more types of representations of intracardiac electrical behavior (e.g., transmembrane potentials, representations of activations and/or repolarizations, etc.) based partly or solely on a patient's ECG. For example, the trained model 40 may be used to generate a cardiac activation map image, and/or a record of the patient's transmembrane potentials over time, based partly or solely on the patient's 12-lead or other ECG. As shown in FIG. 1 and mentioned above, additional patient data such as gender, heart geometry, etc., if known, may also be provided to the trained model 40 in some embodiments. Significantly, the trained model 40 is capable of reconstructing the patient's intracardiac electrical behavior with a reasonable degree of accuracy without the need for any special medical equipment, and without the need for the patient to obtain a CT scan, MRI, X-Ray, or other medical image. For instance, a recently or newly acquired ECG of an emergency room patient may be used to rapidly (e.g., in less than 2 minutes after an ECG is obtained) generate an activation map that can be used to assess the cause of an arrhythmia. In some embodiments, the representation of intracardiac electrical behavior may be generated and displayed to a clinician substantially in real time as the ECG is acquired from the ECG leadset.

In the embodiment illustrated in FIG. 2, the trained model 40 is part of an intracardiac electrical reconstruction system 42 that also includes a visualization and reporting software component 44 for generating one or more types of images or reports. As illustrated, the trained model 40 may include, or may receive input from, an ECG feature extractor 46 that extracts features from the patient's ECG by analyzing the raw or preprocessed ECG data. The feature extractor 46 may be identical to an ECG feature extractor used for model training, and may include a wavelet decomposition component. Although not illustrated in FIG. 2, the intracardiac electrical reconstruction component 42 may also perform one or more of the other types of ECG preprocessing mentioned above (ECG normalization, removal of atrial contribution, etc.). In the case of a neural network, the weights of the trained model are applied to the extracted features to generate output data (e.g., intracardiac electrical behavior features that can be converted to transmembrane voltages at various locations and points in time) representing the patient's intracardiac electrical behavior. The intracardiac electrical reconstruction system 42 may be implemented as a general-purpose computer, such as a laptop, PC or server, programmed with software.

In some embodiments, the trained model 40 generates a record of the transmembrane voltages at various cardiac locations as a function of time. The trained model may generate the transmembrane voltages by mapping extracted ECG features to intracardiac electrical behavior features (activation time, repolarization time, activation potential duration, etc.), which may be converted into voltage waveforms. The visualization and reporting component 44 then converts this transmembrane voltage data into one or more images, videos, graphs, charts, or other records for presentation to clinicians; examples include a cardiac activation map, a video showing the progression of the transmembrane voltages over time, waveforms of specific transmembrane voltages (see FIG. 11), and charts or tables summarizing an automated analysis of the transmembrane voltage data. In some embodiments, the trained model 40 predicts transmembrane voltages at specific cardiac locations (see FIGS. 5 and 6, discussed below) and points in time, and the visualization and reporting component 44 (or some other component of the reconstruction system 42) applies an interpolation algorithm to this data to generate transmembrane voltage data for other cardiac locations.

The task of making the trained model 40 available to clinical facilities may be accomplished in various ways. For example, the trained model may be provided to clinical facilities as an executable file or library that can be installed and executed locally by such facilities. As another example, the trained model may be made accessible over a network as a service, such as a web service, to which the medical facilities transmit ECGs for analysis. Ordinarily, the computational resources needed for training far exceed those needed to apply the trained model. Thus, the training process may be performed, e.g., using a supercomputer or a cloud-based or other array of servers, while the reconstruction task may be performed, e.g., on a single general-purpose computer or computing node. As mentioned below, specialized hardware, such as specialized neural network chips, may optionally be used to accelerate the training and/or reconstruction process.

2. SIMULATION-BASED GENERATION OF TRAINING DATA

Figure 3:
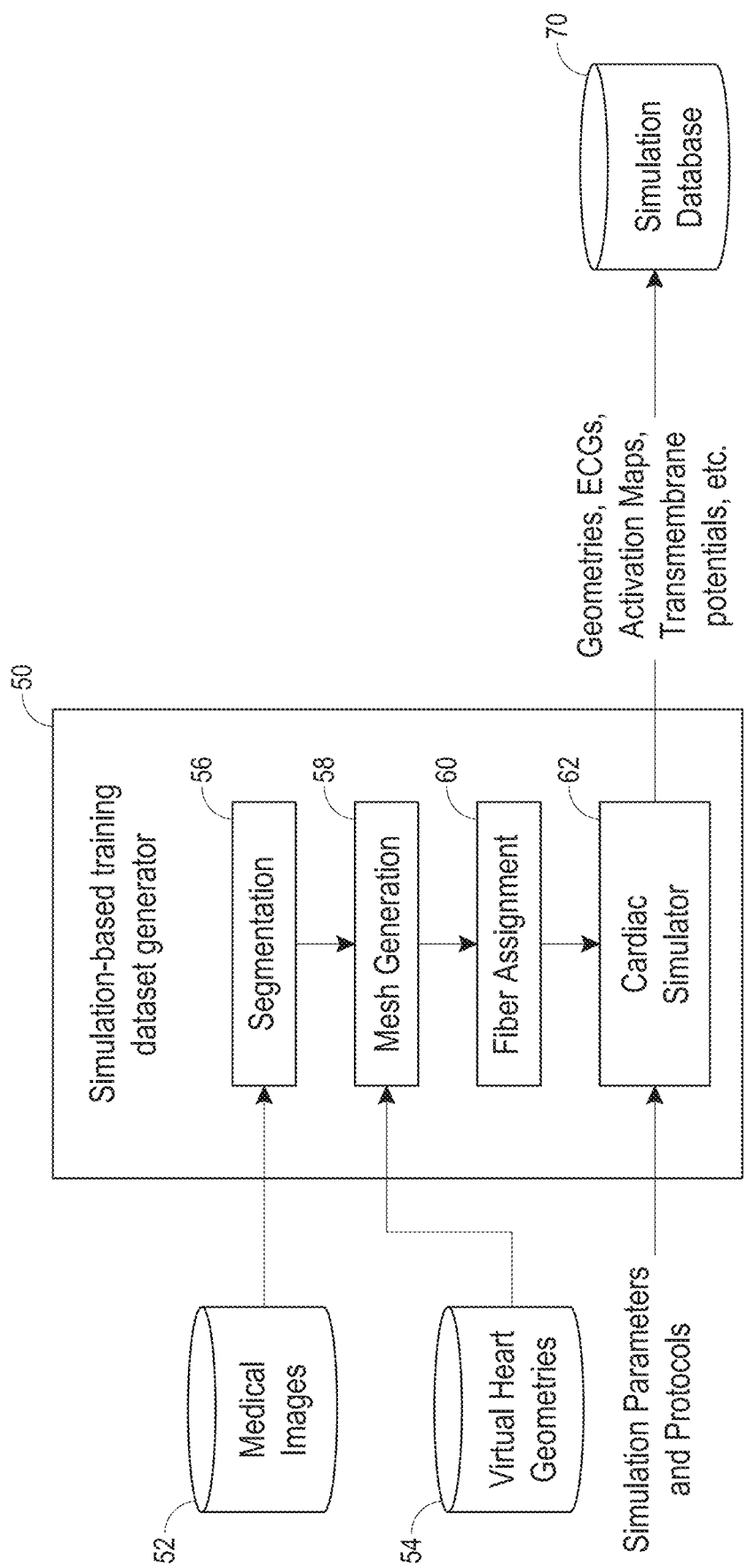
FIG. 3 illustrates a simulation-based process for generating training data according to a preferred embodiment.

FIG. 3 is a flow diagram illustrating a process used by a simulation-based training dataset generator 50 to generate training data according to a preferred embodiment. In the illustrated embodiment, the training dataset generator 50 uses a database of medical images 52, and a database of virtual heart geometries 54, as sources of simulation data, although only one of these two sources may be used in some embodiments. The medical images may include 2D and/or 3D data showing the spatial orientations and layouts of hearts and other organs of a variety of patients (ideally many thousands). Examples of patient images that may be used include cardiac MRI scans, CT scans, X-rays, echocardiograms and PET scans. No actual ECG data or intracardiac electrical activity data of these patients is needed.

Figure 4:
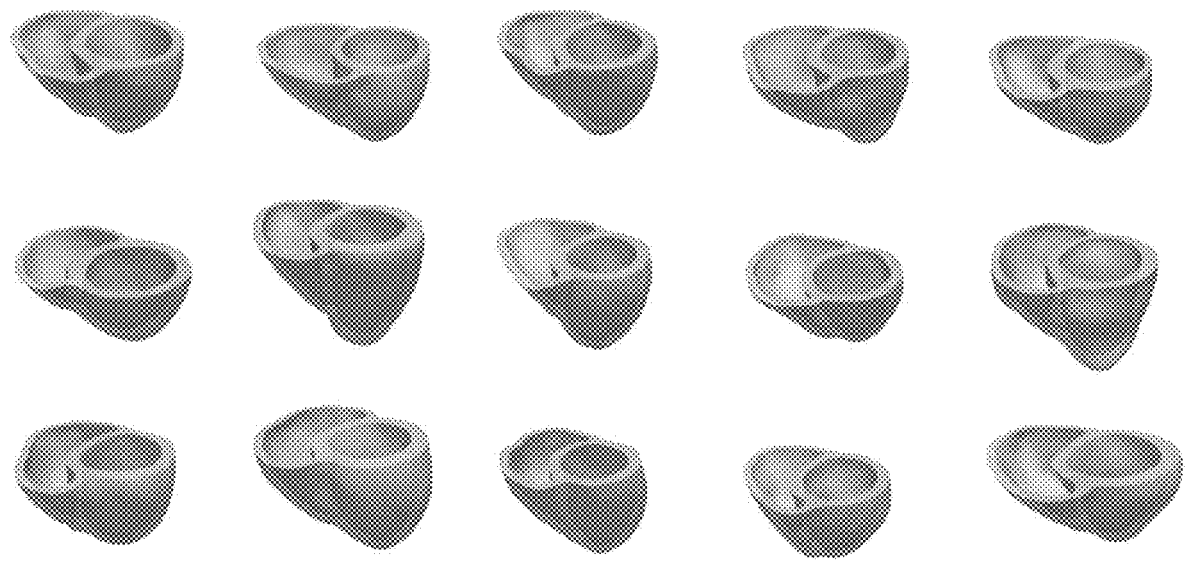
FIG. 4 illustrates a set of heart geometries that may be used in the simulation-based process of FIG. 3.

The virtual heart geometries may be obtained from a publicly accessible database. These geometries may be selected to model inter-subject variability in anatomical morphology and ventricular thickness. As one example, the fifteen bi-ventricular geometries shown in FIG. 4 may be used. These geometries can be sampled from probability distributions describing the range of physically plausible geometries encountered in human anatomy (Nicolas Duchateau, et. al, "Model-based generation of large databases of cardiac images: synthesis of pathological cine mr sequences from real healthy cases," *IEEE transactions on medical imaging,* 37(3):755-766, 2017, referenced again below).

As illustrated by the segmentation block 56 in FIG. 3, if medical images are used, each medical image is segmented to specify the organs corresponding to specific regions of the image. Examples of segmentation include taking a CT scan and labeling every organ in the body with an individual scalar value, or taking an echocardiogram and delineating the cardiac tissue from the rest of the tissue. The segmentation process may be performed automatically by software or manually by human operators. The primary purpose of segmentation is to effectively extract the portion of the image corresponding to the patient's heart. If no medical images are used, the segmentation block 56 may be omitted.

As illustrated by the mesh generation block 58 in FIG. 3, each segmented image, and/or each virtual heart geometry (if virtual heart geometries are used), is converted into a mesh representation suitable for computational analysis. Each mesh is preferably a volume in 3D space represented as a collection of 3D primitives (e.g., cubes, tetrahedra, closed polyhedrons), 2D primitives (such as triangles, closed polygons, etc.), 1D primitives such as segmented lines, and 0D primitives such as points. Examples of meshing include constructing an unstructured finite element mesh to represent the heart and all of the organs in a patient's torso, or a structured regular gird overlaid on the area of interest. Individual mesh primitives can be assigned different properties depending on the label assigned during the segmentation phase. The mesh generation task can be performed using commercially available software programs such as TetGen from WIAS Software or Trelis from csimsoft.

As illustrated by the fiber assignment block 60 in FIG. 3, the next phase of the process involves augmenting the mesh representations of the hearts with data representing the cardiac fibers. This task can be accomplished by deforming one or more atlas hearts into the patient's geometry (or into a virtual heart geometry). Additionally or alternatively, the cardiac fibers may be assigned using a rules based algorithm, such as the algorithm described in Bayer, J. D., R. C. Blake, G. Plank, and N. A. Trayanova. 2012, "A novel rule-based algorithm for assigning myocardial fiber orientation to computational heart models," Annals of Biomedical Engineering 40 (10): 2243-54, the disclosure of which is hereby incorporated by reference.

As further shown in FIG. 3, the meshes with assigned fibers are provided to a cardiac simulator 62, which is used to simulate cardiac electrical behavior. Examples of suitable cardiac simulators include Cardiod from Lawrence Livermore National Laboratory, Chaste from Oxford, and Cardiac Arrhythmia Research Package (CARP). In some embodiments, a mechanical simulator may also be used. The cardiac simulations can be carried out via discretizations of the bidomain method, the mododomain method, the pseudo-bidomain method, the eikonal equations, or can use cellular automata to approximate the propagation of cardiac wavefronts spatially. These propagation patterns can then be used to solve for the electrical potential for the entire torso, using various organ conductivities for each segmentation label carried over from the meshing phase of the process. The propagation and electric potentials can be found together at the same time, or the problem can be split so that propagation can be solved first and torso potentials can be solved later. As illustrated in FIG. 3, simulation parameters and protocols may be varied to perform simulations over a variety of initial electrical conditions and pacing protocols. An example of a simulation parameter that may be varied is fiber conductivity, which may vary based, for example, on the patient's degree of hydration. Example protocols include pacing the heart in each of the AHA 20 locations with standard S1 S2 paces, manually depolarizing regions of tissue, and running all of the above simulations under a variety of both healthy and diseased (such as heart failure or infarct) states.

Figure 5:
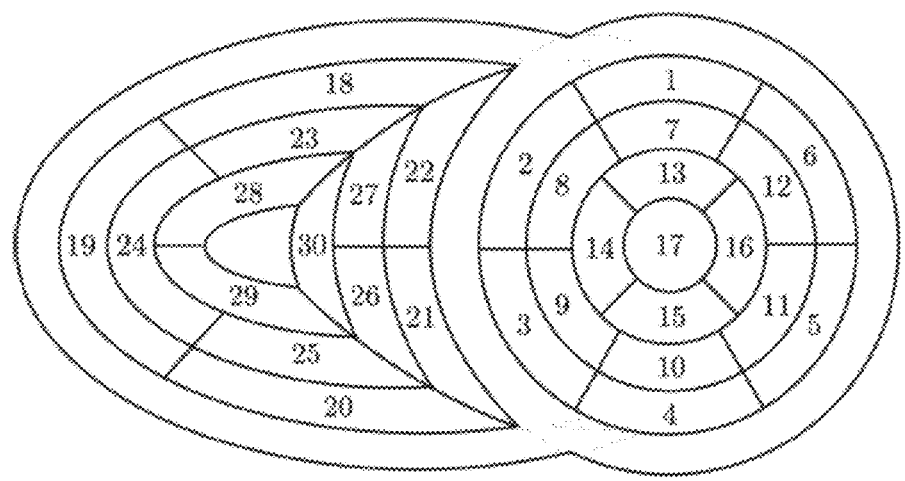
FIG. 5 illustrates an example of a set of endocardial points used for simulation.
Figure 6:
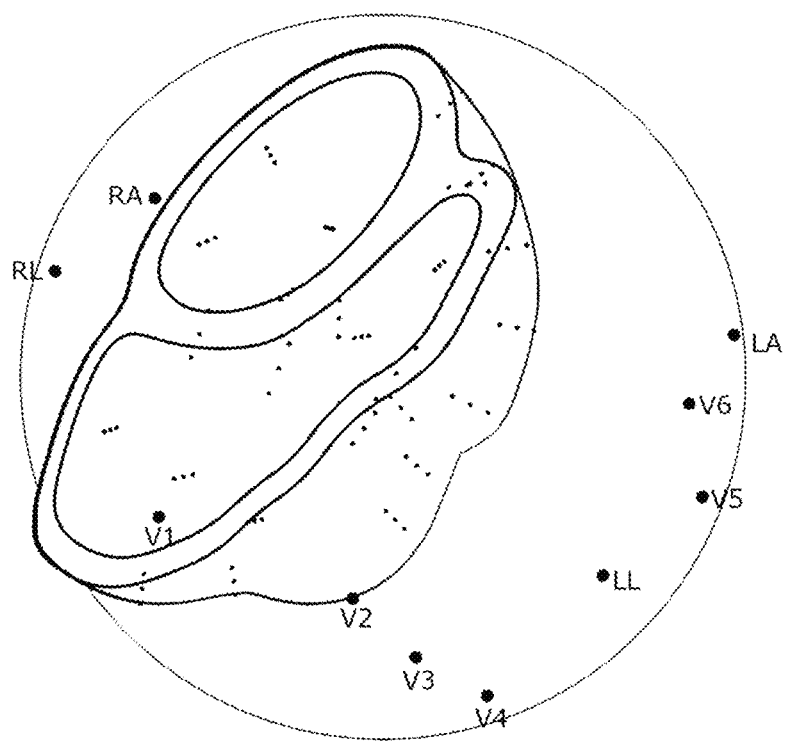
FIG. 6 illustrates pECG electrode locations, and transmembrane voltage sampling locations, used in one embodiment.

During each simulation, a simulated ECG may be generated by sampling well-defined points on the surface of the torso. These points may be determined automatically or selected manually. In addition, data representing transmembrane potentials, activations and repolarizations may be collected. This may involve downsampling the electrical behavior into a coarse mesh by taking measurements at selected points corresponding to anatomical landmarks. FIG. 5 illustrates thirty manually selected endocardial locations that may be used. Seventy-five corresponding points for measuring transmembrane voltages are shown in FIG. 6 as the small dots. Each location in FIG. 5 corresponds to either three locations in FIG. 6 (two outer wall locations plus a location within the wall) or to two locations in FIG. 6 in the case of septum locations. FIG. 6 also shows pseudo ECG (pECG) electrode locations that may be used to generate the simulated ECGs. Rather than using pECG, a full heart-torso coupled problem can be solved for each time-step.

In one embodiment, the transmembrane voltage recording points used for simulation are also the points at which transmembrane voltages are predicted or inferred during reconstruction of a patient's intracardiac electrical behavior. An interpolation algorithm may be used to estimate potentials at other locations in the heart.

As shown in FIG. 3, the output of the simulations is stored in a simulation database that may be used for model training. For each patient or patient geometry, this data may, for example, include the following: (1) simulated ECGs, (3) the downsampled intracardiac electrical behavior corresponding to each ECG, (3) information about the disease state for each ECG, and (4) global statistics corresponding to each ECG, such as patient size, distance of internal organs, orientation of the heart, gender, etc.

Additional details of how the cardiac simulations may be performed are described in U.S. Patent Pub. 2017/0161896, the disclosure of which is hereby incorporated by reference.

The processes shown in FIGS. 1-3 may be embodied in executable code (program instructions) executed by one or more computing systems, each of which includes one or more computing devices having a hardware processor coupled to a memory. The executable code, and the results of the disclosed processes, may be stored on any suitable type or types of non-transitory computer-readable media (disk drives, solid state memory arrays, optical disks, etc.). In some embodiments, different components (hardware and software) of the overall system may reside remotely from each other. As is known in the art of machine learning, in some embodiments specialized hardware may be used to accelerate the training process and/or the process of translating an ECG into a representation of intracardiac electrical activity. For example, specialized neural network processors or chips may be used to accelerate one or both processes.

3. EXPERIMENTATION AND TEST RESULTS

This section 3 describes specific experimentation performed by Lawrence Livermore National Laboratory to test and validate the above-described processes.

A comprehensive database of computational experiments was created in the course of this work. Each experiment consists of intracardiac transmembrane voltage recordings and ECG signal pairs. Details on the simulation settings, such as the mathematical models, the anatomical geometries and the parameter variations, are presented in the following subsection. Details on the neural network architectures used for learning the inverse reconstructions are provided in subsection 3.2.

3.1 Building a Database of Clinical Cardiac Simulations

Cardiac simulations were carried out using Cardioid, a multiscale cardiac simulation software package developed at Lawrence Livermore National Laboratory (LLNL). Cardioid uses a finite volume method with explicit time stepping to solve the monodomain model, a system of reaction-diffusion equations describing the spatiotemporal evolution of the transmembrane voltage within the myocardium. These equations are coupled with cell models that describe the dynamics of ionic species through the cell membrane. The cell models proposed in Kirsten H W J Ten Tusscher and Alexander V Panlov, "*Alternans* and spiral breakup in a human ventricular tissue model," American Journal of Physiology-Heart and Circulatory Physiology, 291(3): H1088-H1100, 2006, were used for endocardial, midmyocardial, and epicardial cells respectively.

The monodomain equations were solved in real bi-ventricular cardiac domains. The patient specific geometries were obtained from the publicly available database (see Nicolas Duchateau, et. al, "Model-based generation of large databases of cardiac images: synthesis of pathological cine mr sequences from real healthy cases," *IEEE transactions on medical imaging*, 37(3):755-766, 2017), and were generated using original MR images from the Stacom 2011 challenge. Meshes were preprocessed to make them compatible with the Cardioid solver and resolved to a 200 µm resolution (see FIG. 4). Myocardial fiber orientations were assigned based on the algorithms in the above-referenced paper titled "A novel rule-based algorithm for assigning myocardial fiber orientation to computational heart models."

The high-resolution simulations of the transmembrane voltages inside the heart were used to compute the synthetic ECG signals. To reconstruct the ECG signal, a full heart-torso coupled problem can be solved for each time-step as is known in the art. Alternatively, a pseudo-ECG approach can be followed as described in Robert Plonsey and Roger C Barr, *Bioelectricity: a quantitative approach*, Springer Science & Business Media, 2007. The latter was used in this work. The locations of the pseudo-ECG electrodes were chosen based on locations derived from an existing torso mesh and then normalized to a 100 mm radius around the center of each mesh (see FIG. 6).

The morphology of the ECG signal is sensitive to the endocardial initial stimulus. In this work, activation patterns were extracted from Dirk Durrer, et al., "Total excitation of the isolated human heart," *Circulation*, 41(6):899-912, 1970], and Louie Cardone-Noott, et al., "Human ventricular activation sequence and the simulation of the electrocardiographic qrs complex and its variability in healthy and intraventricular block conditions," *EP Europace*, 18(suppl 4):iv4-iv15, 2016. To retrieve physiological T wave morphology in the ECG signals, apex-to-base action potential duration (APD) heterogeneity and transmural APD heterogeneity were included within the ionic models. In addition, the methods proposed in Martin J Bishop and Gernot Plank, "Bidomain ECG simulations using an augmented monodomain model for the cardiac source," *IEEE transactions on biomedical engineering*, 58(8):2297-2307, 2011, were used to account for the bath loading effects over the surfaces of the heart.

For the recording of the transmembrane voltages inside the heart, 30 points were selected by hand for each mesh; 17 endocardial points were selected in the left ventricle (LV), corresponding to standard locations established by the American Heart Association (AHA), and 13 points were selected in the right ventricle (RV), according to Liang Zhong, et al., "Right ventricular regional wall curvedness and area strain in patients with repaired tetralogy of fallot," *American Journal of Physiology-Heart and Circulatory Physiology*, 302(6):H1306-H1316, 2011. See FIG. 5 for a schematic representation of the points over a Bull's-eye display of the heart. From these 30 points, 20 wall-exterior points were programmatically identified based on minimum distances from the hand-selected endocardial points, and 25 mid-myocardial points were then found through interpolation. For each simulation performed, simulated transmembrane voltages were recorded for each of the 75 epicardial/midmyocardial/endocardial points. These transmembrane voltages were paired with the ECGs collected above for use in the machine learning classier.

Human ventricular activation and ECG data exhibit a high level of morphological variability depending on physiological and pathophysilogical factors. To reproduce this variability and enrich the dataset of activation-ECG pairs, the following combinations of parameters were explored:

(1) A suite of 15 clinical bi-ventricular geometries was considered to model inter-subject variability in anatomical morphology and ventricular thickness. See FIG. 4.

(2) A library of 29 clinically-inspired activation patterns was designed to account for variations across patient Purkinje systems. For each activation pattern, activation times over the previously identified 30 endocardial points were chosen according to the distributions presented in Dirk Durrer, et al., "Total excitation of the isolated human heart," *Circulation*, 41(6):899-912, 1970, and Louie Cardone-Noott, et al., "Human ventricular activation sequence and the simulation of the electrocardiographic qrs complex and its variability in healthy and intraventricular block conditions," *EP Europace*, 18(suppl 4):iv4-iv15, 2016.

(3) A set of 3 different combinations of tissue conductivities (longitudinal, traversal and normal) was considered. Starting from the original values reported in Steven A Niederer, et al., "Verification of cardiac tissue electrophysiology simulators using an n-version benchmark," *Philosophical Transactions of the Royal Society A: Mathematical, Physical and Engineering Sciences*, 369(1954):4331-4351, 2011, the library was designed so that 3:1, 4:1 and 6:1 ratios between longitudinal and transverse conduction velocities were achieved. These parameters were tested and exhibited conduction velocities that where within physiological ranges.

(4) In addition to the original $G_{Kr}$ value proposed by Kirsten H W J Ten Tusscher and Alexander V Panfilov, "*Alternans* and spiral breakup in a human ventricular tissue model," *American Journal of Physiology-Heart and Circulatory Physiology*, 291(3):H1088-H1100, 2006, for the cell model, two variations were considered: 0% (blocked) and 50% original value. This parameter controls the rapid delayed rectifier current in the cell membrane and is known to affect APD.

(5) Basic Cycle Lengths (BCL) of 600 ms and 1000 ms were considered to produce different initial states for the cell models. Initial states computed with different BCL affects APD.

(6) Randomized samples over the space of inner activation points (75 points inside the myocardium) were considered to capture early activation and pathological scenarios.

All simulations were performed for 500 ms of simulation time with 200 μm resolution meshes and a time-step of 5 vs. The ECG and transmembrane voltages were recorded at a resolution of 1 ms. All variations in the cell model parameters (apex-to-base and transmural APD heterogeneity, GKr and BCL) were pre-simulated with 100 beats in a single cell simulation in order to reach dynamic steady state.

In total, 16140 organ-level simulations were conducted. Simulations were performed at LLNL's Lassen supercomputer, concurrently utilizing 4 GPUs and 40 CPU cores.

3.2 Machine Learning for Intracardiac Electroimaging

The simulation study described above produced pairs of 12-by-500×1 ms ECG signals and 75-by-500×1 ms transmembrane voltage signals. For the sake of notation, those signals are represented as matrices $ECG \in R^{12 \times 500}$ and $V \in R^{75 \times 500}$, respectively. The activation time vector $ACT \in R^{75}$, corresponding to the initial activation time at each myocardium recording location, is defined as $ACT_i = \min_j V_{ij} > 0$. Two machine learning tasks were considered in this work: (1) Activation map reconstruction (Task I): Given $ECG \in R^{12 \times 500}$, reconstruct $ACT \in R^{75}$; (2) Transmembrane potential reconstruction (Task II): Given $ECG \in R^{12 \times 500}$, reconstruct $V \in R^{75 \times 500}$.

These tasks can be regarded as sequence-to-sequence prediction problems, where the goal is to transform a 500-length sequence of 12 dimensional vectors into a sequence of 75 dimensional vectors. The length of the output vector is 1 for Task I (sequence transduction problem) and 500 for Task II (regression per time step problem). Note that Task II involves reconstructing 500 times more information than Task I.

There have been several recent breakthroughs in modeling sequence-to-sequence problems using machine learning, particularly for language translation and text-to-speech synthesis. The traditional approach is to use recurrent neural networks (RNNs), where the long short-term memory (LSTM) model plays a prominent role. These are powerful models that can keep track of long-term dependencies in the input sequences but they are usually difficult to train. Alternatives based on 1D convolutional neural networks (CNNs) have recently been proposed in the literature. These models are more computationally and memory efficient compared to RNNs and yet they can outperform their results. Variants in this space include temporal convolutional neural networks (TCNN) and autoregressive models. Any one or more of these neural network architectures, among others, may be used in embodiments of the invention.

For classification and compression of ECG signals, researches have used a variety of architectures: fully connected networks (FCNs), 1D CNNs, 2D CNNs and hybrid approaches combining CNNs and LSTM units. For reconstruction tasks of heart surface potentials, a time-delayed NN may be used to map the real recorded first lead of the ECG to the unipolar surface potential at the right ventricle apex. See Avinash Malik, Tommy Peng, and Mark L Trew, "A machine learning approach to reconstruction of heart surface potentials from body surface potentials," 2018 40*th Annual International Conference of the IEEE Engineering in Medicine and Biology Society* (*EMBC*), pages 4828-4831, IEEE, 2018.

Different network architectures were explored for Tasks I and II, including FCNs, LSTM networks, TCNNs and 1D CNNs. Best results were achieved using 1D CNN architectures inspired by the SqueezeNet model (see Forrest N Iandola, Song Han, Matthew W Moskewicz, Khalid Ashraf, William J Dally, and Kurt Keutzer, "Squeezenet: Alexnet-level accuracy with 50× fewer parameters and <0.5 mb model size," *arXiv preprint arXiv*:1602.07360, 2016). SqueezeNet was originally proposed for image classification as an attempt to produce a high-performance model using as few parameters as possible. It makes intensive use of convolutional kernels of dimension 1 and dimension 3 that squeeze and expand the information through the multiple layers. The model is fully convolutional since the network graph does not contain any dense layer. Two different networks were considered in this work:

Network I (for Task I): Network I was constructed using SqueezeNet (with 1 dimensional kernels) with a stride of size 2 in the first convolutional layer and maxpooling layers to progressively reduce the temporal dimension. Additional convolutional layers were added at the end to reduce the output dimension to R75. The size of the final network is less than 6 MB.

Network II (for Task II): Network II was constructed using SqueezeNet (with 1 dimensional kernels). Additional convolutional layers were added at the end to produce outputs of dimension R75×500. The size of the final network is less than 40 MB.

Note that the considered network architectures allow for both temporal and spatial information coming from the ECG signal to be combined and reorganized in a nonlinear way. This is in agreement with the well-known fact that some sort of temporal information should be considered to alleviate the common problems in inverse reconstruction problems. For training the networks, each $ECG \in R^{12 \times 500}$ tensor was normalized so that $\max_j(ECG_{ij}) - \min_j(ECG_{ij}) = 1$, $\forall i \in \{1, \ldots, 12\}$. To train Network II, each $V \in R^{75 \times 500}$ was normalized so that the value range was [0,1]. The dataset was randomly split into training and validation subsets containing 95% and 5% of the samples, respectively. The networks were implemented in Python using the PyTorch library. Learning was performed over one GPU at LLNL's Lassen supercomputer.

3.3 Activation Map Reconstruction (Task I)

Figure 7:
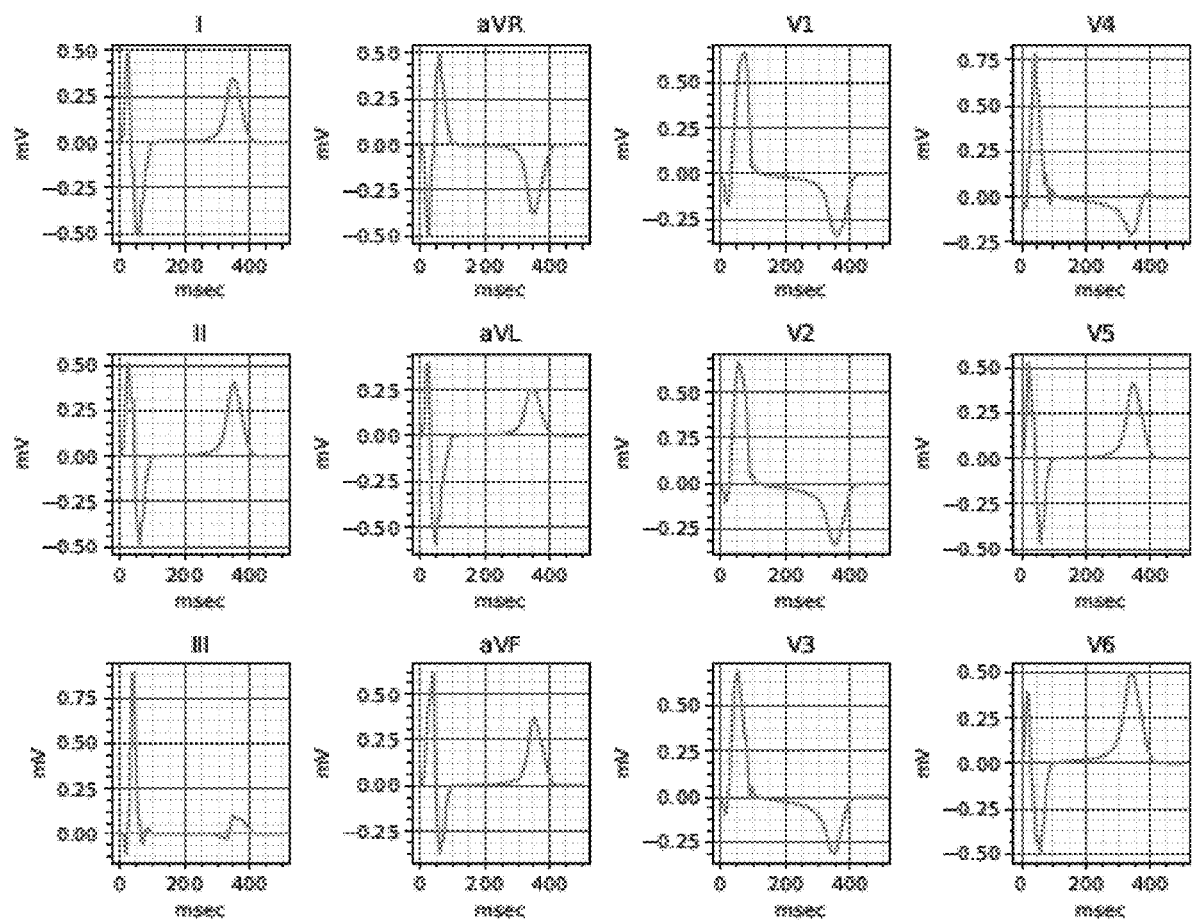
FIG. 7 illustrates simulated ECG waveforms used in a validation set.
Figure 8:
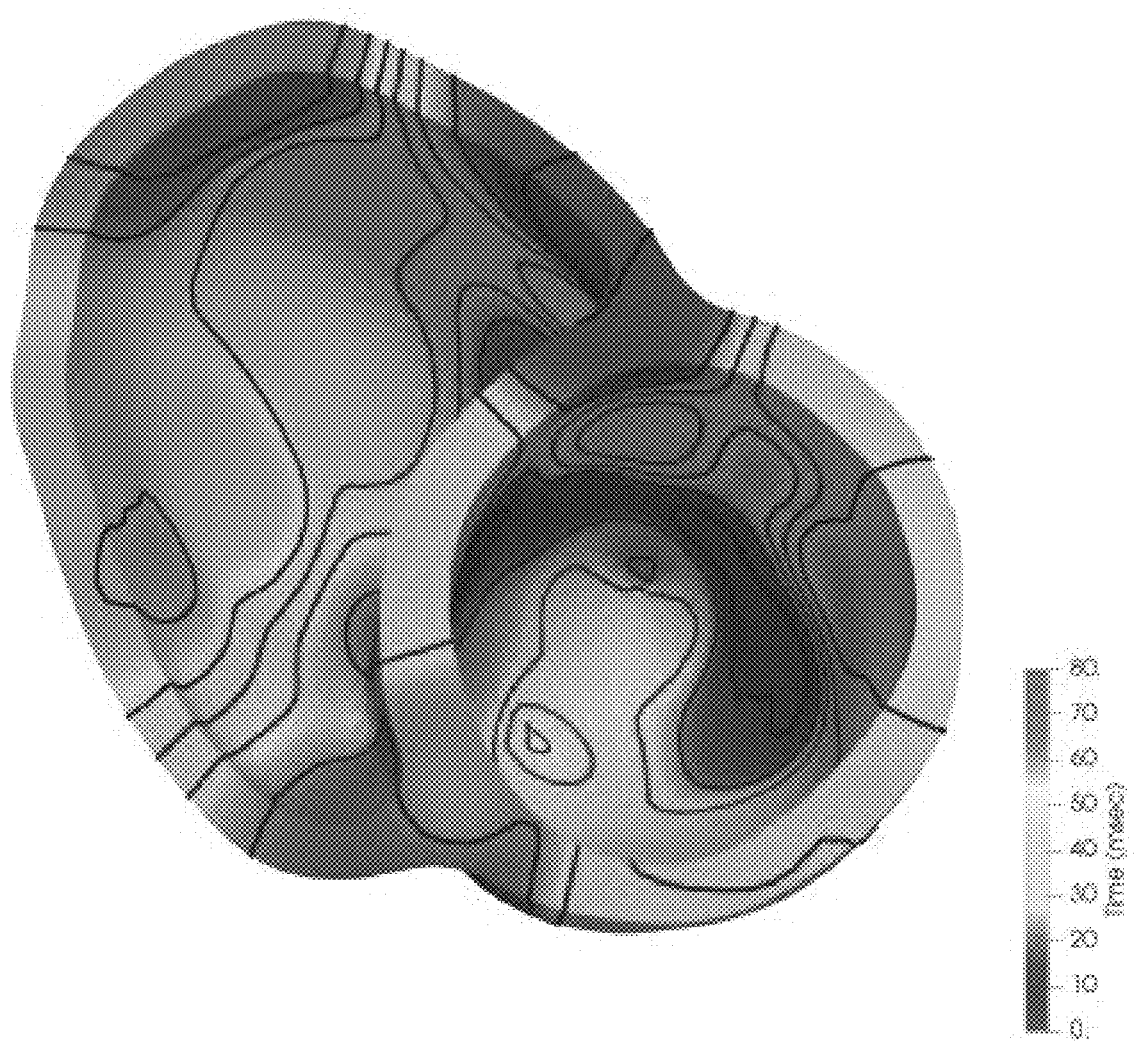
FIG. 8 illustrates a simulated activation map corresponding to the simulated ECG waveforms of FIG. 7.
Figure 9:
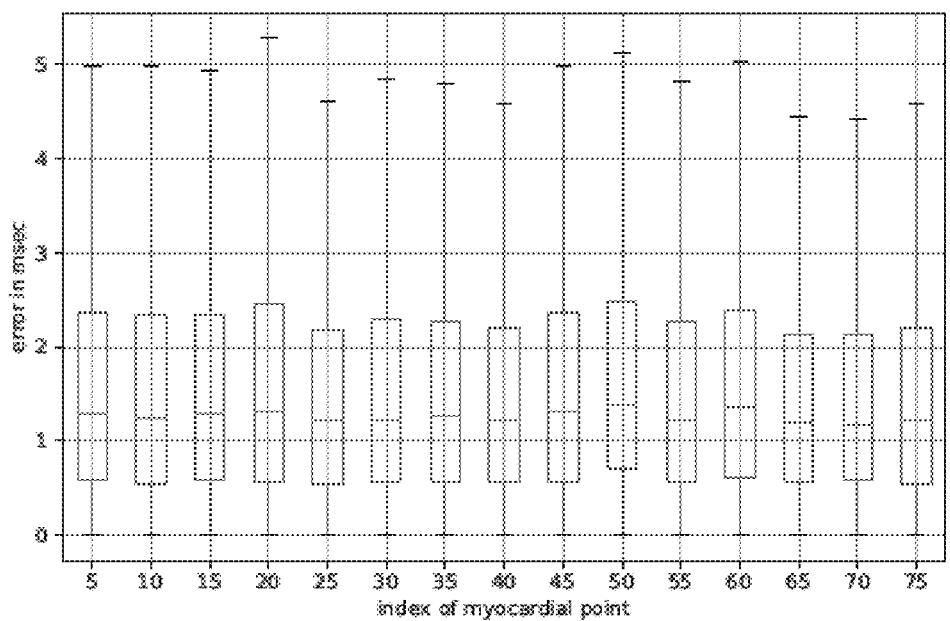
FIG. 9 illustrates errors in activation times for a selection of 15 recording points over all the validation set of FIGS. 8 and 9.
Figure 10:
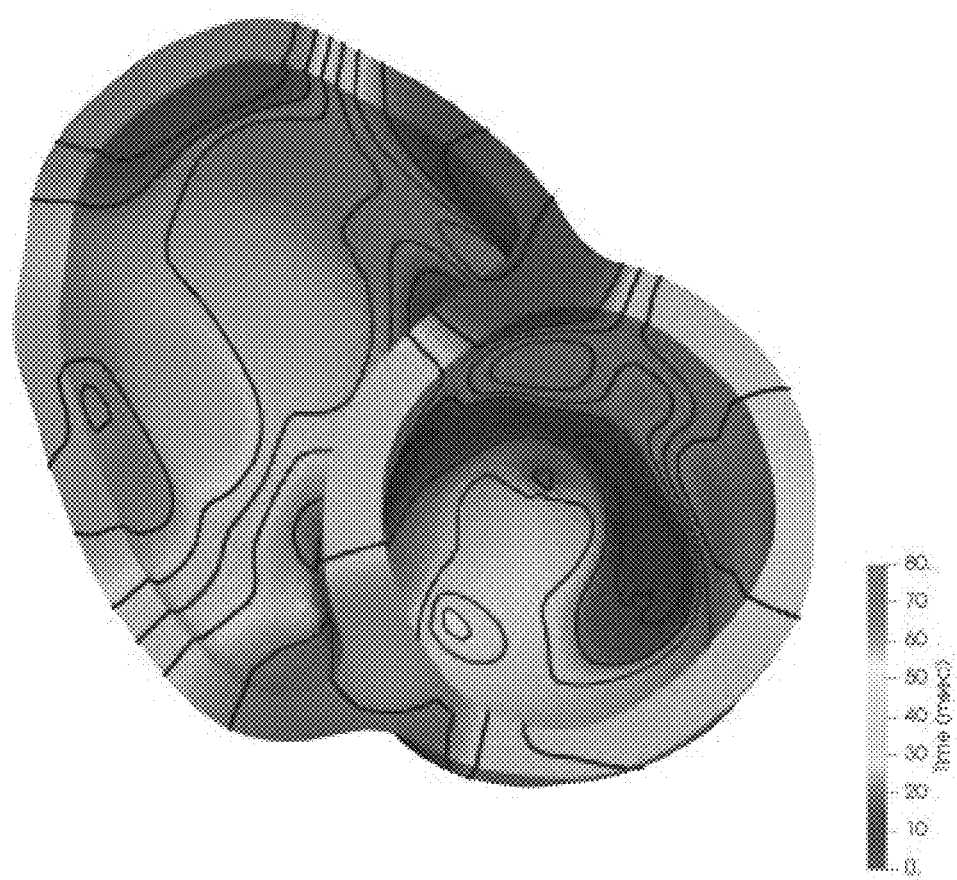
FIG. 10 illustrates a reconstructed activation map corresponding to FIGS. 7-9.

FIGS. 7 and 8 show an example of simulated ECG (FIG. 7) and activation map (FIG. 8) in the validation set. The reconstruction obtained by Network I is shown in FIG. 10. FIG. 9 shows the errors in activation times for a selection of 15 myocardial recording points over the whole validation set. On average, the network incurs an error of 1.7 msec in predicting the activation times at each recording point for all of the validation set.

These results show that Network I is able to reconstruct the activation map over the validation set of simulated data. Recall that these examples have not been seen by the network during training. In particular, the algorithm is able to capture and reproduce both septal and transmural activation times in the cardiac tissue, in contrast with other methods in the literature.

3.4 Transmembrane Potential Reconstruction (Task II)

Figure 11:
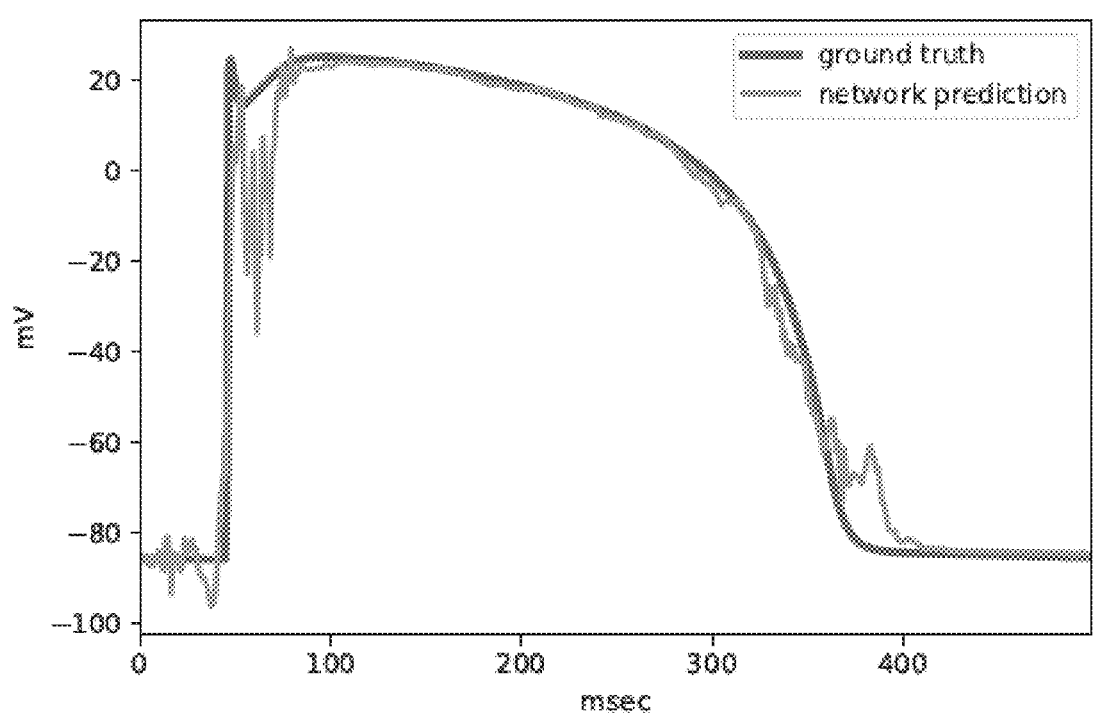
FIG. 11 illustrates a comparison of predicted transmembrane potential (generated during reconstruction) to ground-truth transmembrane potential.
Figure 12:
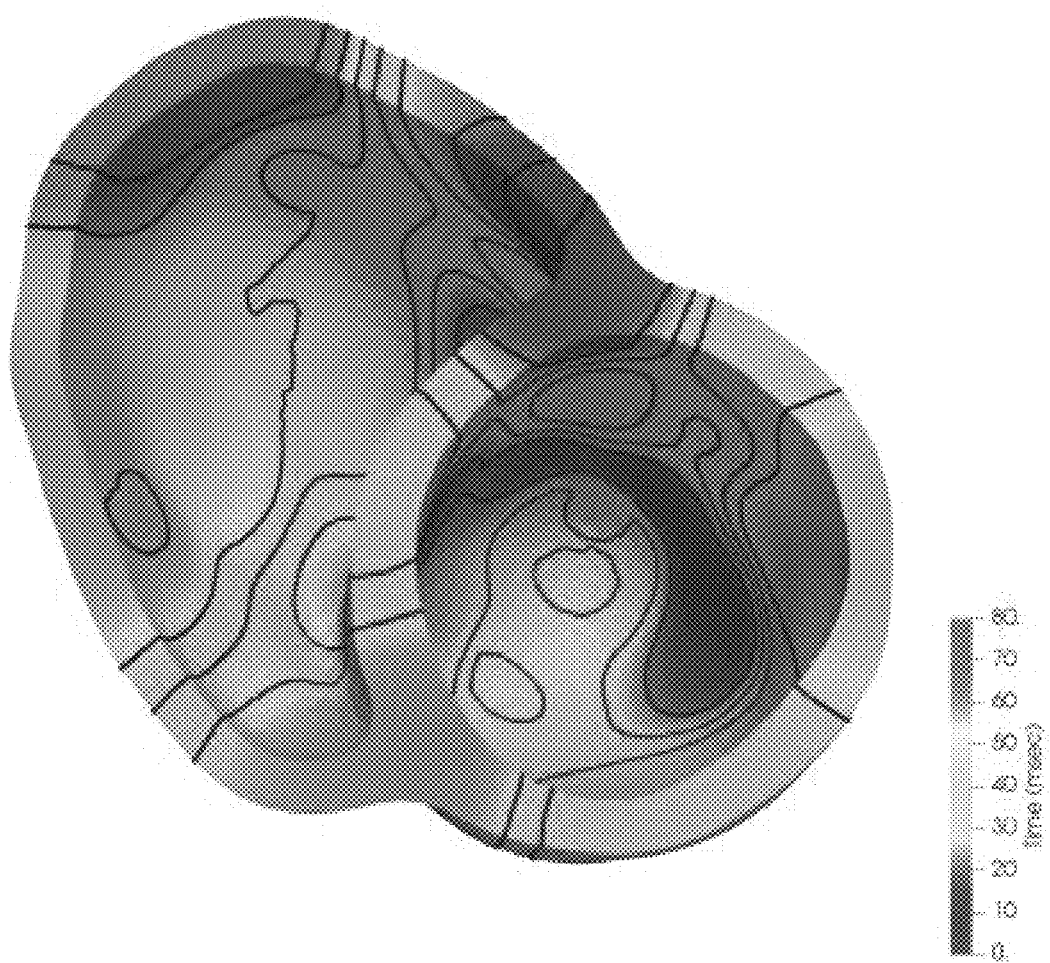
FIG. 12 illustrates a reconstructed activation map.

FIGS. 11 and 12 show the reconstruction results obtained with Network II for the validation ECG in FIG. 7. Recall that this network produces as output the whole tensor $V \in R^{75 \times 500}$. FIG. 11 shows an example of the reconstructed transmembrane voltage compared with the reference simulated result for a chosen myocardial recording point. The corresponding activation time vector $ACT \in R^{75}$ is computed from $V \in R^{75 \times 500}$ and plotted in FIG. 12.

FIGS. 11 and 12 show that the transmembrane voltage reconstruction obtained with Network II contains non-physical oscillations when compared to the simulated data. The activation times are also slightly slower compared to ground truth. Specifically, the mean error in the reconstruction of activation times using Network II for all points in the validation test is 6.5 msec. The error is higher than in Network I. This is not surprising since in this case the reconstruction is not targeting the activation map itself but rather the whole temporal evolution of the transmembrane voltage inside the heart.

With these limitations in mind, Network II is able to capture the gross phenotypical patterns of activation, the morphology of the activation potential including the APD and the complete dynamical evolution of the depolarization and repolarization phases of the cardiac cycle.

Network I can be used when the activation map reconstruction is all what is required. If the complete temporal reconstruction of the depolarization and repolarization phases is needed, Network II can be used.

3.4 Conclusions Reached from Experimentation

The proposed approach offers opportunities for non-invasively stratify patients based on metrics that would otherwise only be available through invasive electro-anatomical mapping studies. The resulting prediction tools do not require any special equipment, work with the standard 12-lead ECG and can be stored and deployed in devices with low memory and processing capabilities. The proposed approach can be improved and adjusted with new data using transfer learning, if desired.

Figure 13:
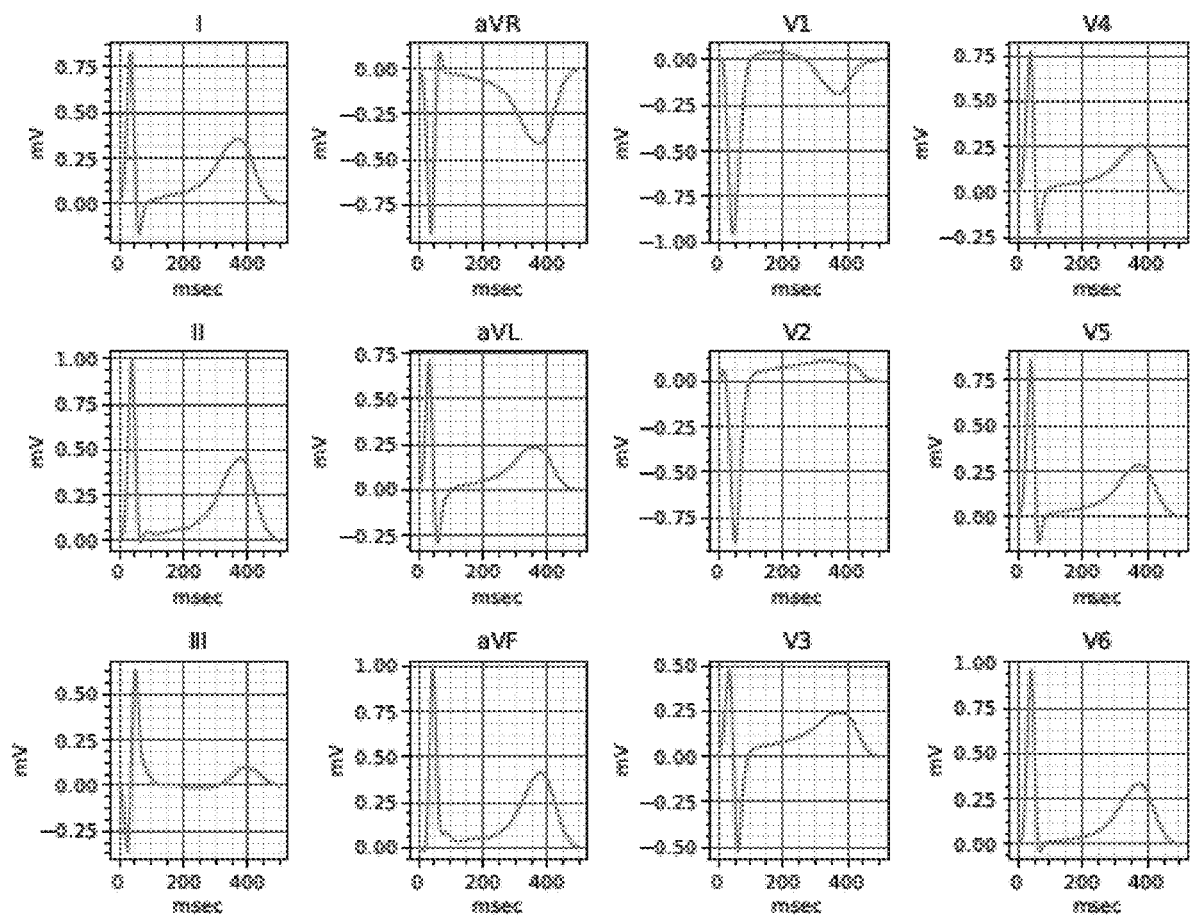
FIG. 13 illustrates actual, normalized ECG data used for validation.
Figure 14:
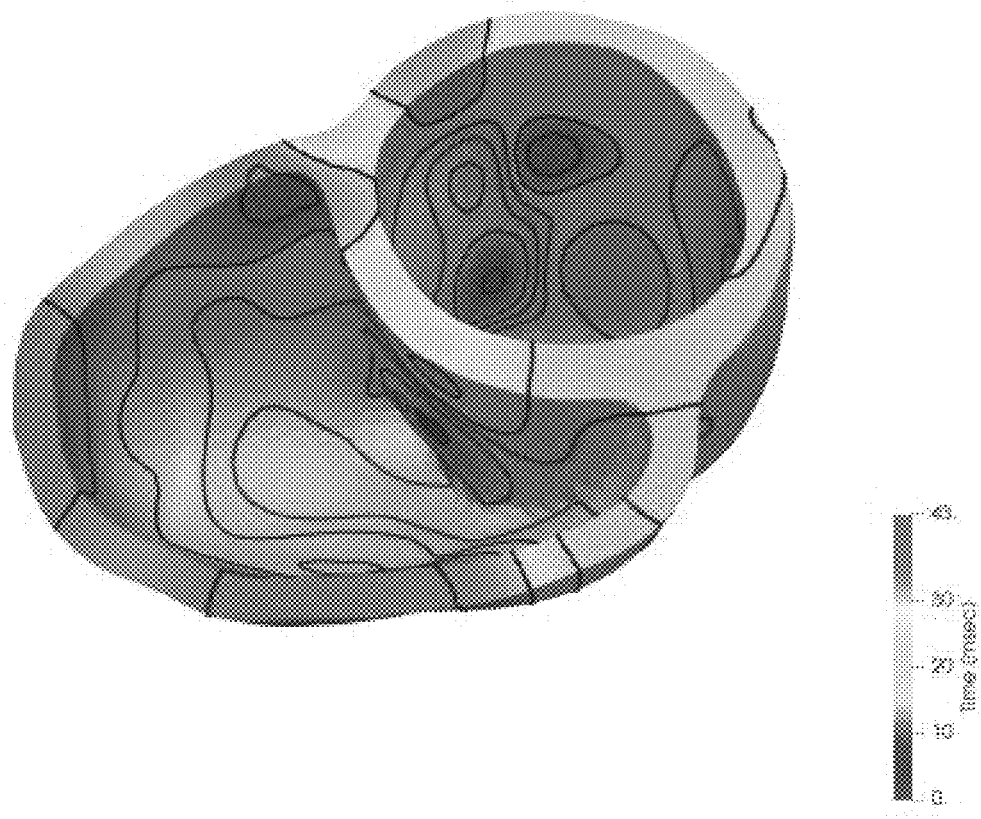
FIG. 14 illustrates an activation map generated using the ECG data of FIG. 13.

As a preliminary validation result, Network I was presented with a real ECG record extracted from the PhysioNet repository. Specifically, the ECG trace was obtained from the record "s03141re" of patient049 over the temporal window [990, 1490] ms. The signal was preprocessed using a de-noising filter and was centered around 0 my. The baseline shift was subtracted from the signal and it was normalized. The results are shown in FIGS. 13 and 14. The resulting activation map morphology and range is within physiological values. Although these results are promising, the network showed non-physiological results for certain ECG signals. This suggests that a larger space of simulated data should be considered to increase the robustness of the method.

The accuracy of the trained models can potentially be improved by using more detailed models (e.g., including the atria geometry) and/or by enlarging the simulated dataset (e.g., to consider more cardiac geometries). A promising idea is to use an atlas model of the heart, so that the heart geometry is parametrized and samples from a virtually infinite range of geometries can be considered. From the machine learning side, a promising idea to improve the reconstruction quality (specially for Network II) is to use an auto-encoder to embed tensor V into a lower dimensional space that would ease the learning problem.

4. CONCLUSION

Although inventive subject matter has been described in terms of certain embodiments and applications, other embodiments and applications that are apparent to those of ordinary skill in the art, including embodiments which do not provide all of the features and advantages set forth herein, are also within the scope of this invention. Accordingly, the scope of the present invention is intended to be defined only by reference to the following claims.

What is claimed is:

1. A process for non-invasively generating a representation of intracardiac electrical behavior of a patient, the process comprising:

receiving an electrocardiogram (ECG) of the patient via an ECG leadset;

extracting a plurality of features of the ECG by analyzing the ECG with an ECG feature extractor;

mapping the plurality of ECG features to a plurality of intracardiac electrical behavior features using a trained machine learning model trained to predict intracardiac electrical behavior based on ECG data, wherein the trained machine learning model comprises a sequence-to-sequence neural network; and converting, by said sequence-to-sequence network, the plurality of intracardiac electrical behavior features into representations of transmembrane voltages over time at each of a plurality of cardiac locations;

said process performed as the ECG is acquired via the ECG leadset.

2. The process of claim 1, wherein the ECG is a 12-lead ECG.

3. The process of claim 1, wherein the trained machine learning model comprises a plurality of layers and comprises weights that reflect detected correlations between ECG features and intracardiac electrical behavior features.

4. The process of claim 1, further comprising converting the plurality of intracardiac electrical behavior features into a cardiac activation map.

5. The process of claim 1, wherein the trained machine learning model is trained, at least partly, with simulated ECGs and simulated intracardiac electrical behavior data obtained from computer-based cardiac simulations.

6. The process of claim 1, wherein the process is performed without use of any medical images of the patient.

7. The process of claim 1, further comprising training the sequence-to-sequence neural network with simulated ECGs and simulated intracardiac electrical behavior data for each of a plurality of cardiac geometries.

8. The process of claim 7, wherein training the sequence-to-sequence neural network comprises:

performing feature extraction on the simulated ECGs and simulated intracardiac electrical behavior data to identify features of the simulated ECGs and features of corresponding intracardiac electrical behavior; and generating model weights that represent correlations between the features of the simulated ECGs and features of the corresponding intracardiac electrical behavior.

9. The process of claim 8, wherein performing feature extraction comprises performing wavelet decomposition of the simulated ECGs.

10. The process of claim 7, further comprising performing validation of the trained machine learning model using actual ECGs and corresponding actual intracardiac electrical behavior of patients.

11. A system for non-invasively generating a representation of intracardiac electrical behavior of a patient, the system comprising:

a computing system comprising one or more computing devices, the computing system configured to implement at least:

an electrocardiogram (ECG) feature extractor configured to analyze an ECG of a patient and to identify a plurality of features of the ECG; and a trained machine learning model trained to predict a plurality of intracardiac electrical behavior features of the patient based on the plurality of ECG features identified by the ECG feature extractor and to convert the plurality of intracardiac electrical behavior features into representations of transmembrane voltages over time at each of a plurality of cardiac locations;

wherein the trained machine learning model is a trained sequence-to-sequence neural network.

12. The system of claim 11, wherein the ECG feature extractor is configured to identify the plurality of features from a 12-lead ECG.

13. The system of claim 11, wherein the trained machine learning model is trained with simulated ECGs and simulated intracardiac electrical behavior data.

14. The system of claim 11, wherein the trained machine learning model comprises a plurality of layers and comprises weights that reflect detected correlations between ECG features and intracardiac electrical behavior features.

15. The system of claim 11, wherein the computing system is further configured to generate a cardiac activation map based on the plurality of intracardiac electrical behavior features predicted by the trained machine learning model.

16. The system of claim 11, wherein the computing system is further configured to implement a model generator that trains the sequence-to-sequence neural network with simulated ECGs and simulated intracardiac electrical behavior data for each of a plurality of cardiac geometries.

17. The system of claim 11, wherein the model generator is configured to train the sequence-to-sequence neural network by a process that comprises:
  performing feature extraction on the simulated ECGs and simulated intracardiac electrical behavior data to identify features of the simulated ECGs and features of corresponding intracardiac electrical behavior; and
  generating model weights that represent correlations between the features of the simulated ECGs and features of the corresponding intracardiac electrical behavior.

* * * * *